United States Patent [19]

Henry

[11] Patent Number: 5,126,141
[45] Date of Patent: * Jun. 30, 1992

[54] COMPOSITIN AND METHOD FOR POST-SURGICAL ADHESION REDUCTION WITH THERMO-IRREVERSIBLE GELS OF POLYOXYALKYLENE POLYMERS AND IONIC POLYSACCHARIDES

[75] Inventor: Raymond L. Henry, Grosse Pointe Woods, Mich.

[73] Assignee: Mediventures Incorporated, Dearborn, Mich.

[*] Notice: The portion of the term of this patent subsequent to Dec. 10, 2008 has been disclaimed.

[21] Appl. No.: 565,770

[22] Filed: Aug. 10, 1990

Related U.S. Application Data

[60] Continuation-in-part of Ser. No. 517,283, May 1, 1990, which is a continuation-in-part of Ser. No. 449,215, Dec. 12, 1989, which is a division of Ser. No. 272,199, Nov. 16, 1988, Pat. No. 4,911,926.

[51] Int. Cl.⁵ .................... A61K 9/107; A61K 47/34; A61K 47/36
[52] U.S. Cl. ................ 424/423; 424/78.37; 424/427; 424/431; 514/944
[58] Field of Search ............... 424/423, 78, 427, 437, 424/78.37

[56] References Cited

U.S. PATENT DOCUMENTS

| | | | |
|---|---|---|---|
| 3,640,741 | 2/1972 | Etes | 106/170 |
| 3,847,155 | 11/1974 | Bernaola | 128/334 |
| 3,947,250 | 3/1976 | Pollack | 435/7 |
| 4,125,608 | 11/1978 | Blum et al. | 514/54 |
| 4,540,407 | 9/1985 | Dunn | 604/292 |
| 4,651,736 | 3/1987 | Sanders | 128/305 |
| 4,795,642 | 1/1989 | Cohen | 424/455 |
| 4,879,062 | 11/1989 | Moore | 514/789 |
| 4,889,722 | 12/1989 | Sheffield et al. | 424/450 |
| 4,895,724 | 1/1990 | Cardinal et al. | 424/418 |
| 4,911,926 | 3/1990 | Henry et al. | 424/426 |
| 4,917,886 | 4/1990 | Asche et al. | 424/81 |

OTHER PUBLICATIONS

Surgery, Gynecology and Obstetrics, Sep. 1971, vol. 133, pp. 497–509 at pp. 502–503.
The Journal of Reproductive Medicine, Jan. 1987, pp. 17–20.
Journal of Surgical Research, vol. 14, No. 4, Apr. 1973, pp. 277–284.
British Journal of Surgery, 1964, vol. 51, No. 5, May.
Annals of the Royal College of Surgeons of England, (1990) vol. 72, 60–63.

Primary Examiner—Thurman K. Page
Assistant Examiner—E. J. Webman
Attorney, Agent, or Firm—Andrew E. Pierce

[57] ABSTRACT

A process and compositons for reducing post-surgical adhesion formation/reformation in mammals following injury to organs situated in mammalian body spaces. Aqueous, thermally reversible gel compositions, preferably at mammalian body fluid pH, comprising a polyoxyalkylene polymer and an ionic polysaccharide are applied to injured areas of the organs situated in body cavities such as, the peritoneal, pelvic, or pleural cavity. The aqueous gels are rendered thermally irreversible upon contact with a counter-ion.

44 Claims, 1 Drawing Sheet

RESISTANCE TO PENETRATION OF POLOXAMER-ALGINATE GEL vs. TEMPERATURE arrow denotes point of introduction of Calcium ions

COMPOSITIN AND METHOD FOR POST-SURGICAL ADHESION REDUCTION WITH THERMO-IRREVERSIBLE GELS OF POLYOXYALKYLENE POLYMERS AND IONIC POLYSACCHARIDES

This is a continuation-in-part of copending application Ser. No. 517,283 filed on May 1, 1990 which is a continuation-in-part of Ser. No. 07/449,215 filed Dec. 12, 1989, which is a divisional application of Ser. No. 07/272,199 now U.S. Pat. No. 4,911,926.

BACKGROUND OF THE INVENTION

1. Field of the Invention

This invention relates to methods and compositions for reducing post-surgical adhesions in the mammalian abdominal or thoracic cavity or other body spaces, whether accidentally or surgically created.

2. Description of the Prior Art

There is a need for a method and composition suitable for use in preventing adhesion formation/reformation in mammals following injury to the organs of the peritoneal, pelvic or plural cavity, or other body spaces, such as subdural, extraocular, intraocular, otic, synovial, tendon sheath, whether accidentally or surgically created.

According to Ellis in a review entitled "The Cause And Prevention Of Post-operative Intraperitoneal Adhesions" in *Surgery, Gynecology and Obstetrics* for Sep. 1971, volume 133, pages 497–509, at pages 502–503, the prevention of adhesions has been the subject of an enormous amount of work since the beginning of this century. According to Ellis, these attempts have included means of preventing the fibrin-coated walls of the intestine from reaching each other by distending the abdomen with oxygen or filling the abdomen with saline solution, paraffin, olive oil, lanolin, concentrated dextrose solution, macromolecular solutions of all sorts, and silicones.

Menzies and Ellis in a article entitled "Intestinal Obstruction from Adhesions—How Big is the Problem?", *Annals of the Royal College of Surgeons* of England, volume 72, pages 60–63, 1990 reported adhesions findings in 10.4% of 115 patients with first-time laparotomies while 93% of 210 patients had intra-abdominal adhesions due to previous surgery. Admission for intestinal obstruction was made for 0.9% of 28,297 general surgery patients while 3.3% of 4,502 laparotomy patients were admitted for adhesive obstruction. These data emphasize the magnitude of readhesion after adhesiolysis or from subsequent surgical procedures. The authors state on p. 62, that there is currently no effective treatment that prevents the recurrence of lysed adhesions.

Caspi, Halperin, and Bukovsky in an article entitled "The Importance of Periadnexal Adhesions in Reconstructive Surgery for Infertility" appearing in *Fertility and Sterility* for Mar. 1982, volume 31, number 3, pages 296–300, at page 299 indicate that despite experimental and clinical efforts in the prevention of adhesion formation following surgery, no major advances have thus far been achieved. The authors discuss the use of post-operative intraperitoneal installation of a mixture of hydrocortisone acetate (a glucocorticoid), promethazine, and ampicillin. As an alternative method of treatment, a low molecular weight dextran (a branched polysaccharide composed of glucose units) was also instilled intraperitoneally in another group of patients. The authors conclude that the intraperitoneal installation of high doses of glucocorticoids combined with early hydrotubations seems to be a worthwhile method.

Musich and Behrman in an article entitled "Infertility Laparoscopy In Perspective: Review of 500 Cases" appearing in *The American Journal of Obstetrics and Gynecology* for Jun. 1, 1982, pages 293–303, at page 300 in the discussion section of the article disclose that there is a need to prevent adhesions subsequent to surgery in view of a study of 35 patients which indicated that 30 of these patients having previous tuboplasties had severe adhesions, one-third of which were judged to be inoperable.

High molecular weight dextran either alone or in combination with dextrose has been used in the prevention of peritoneal adhesions subsequent to surgery. Dextran is clinically standardized to a low molecular weight of about 75,000 by partial hydrolysis and fractional precipitation of the high molecular weight particles which normally have molecular weights of up to 200,000. Dextran is a polymer of glucose which has a chain-like structure and is produced from sucrose by Leuconostoc bacteria. In articles appearing in *Fertility and Sterility*, volume 33, number 6, Jun. 1980, pages 660–662, Holtz, Baker, and Tsai and volume 34, number 4, Oct. 1980, pages 394–395, by Holtz and Baker, results are reported of the adhesion reducing effects of a 32% (aqueous) solution of dextran 70 containing 10% dextrose (sold under the trade name HYSKON by Pharmacia, of Piscataway, N.J.). Holtz et al postulate several mechanisms of action in the prevention of peritoneal adhesions utilizing HYSKON including a simple mechanical separation of adjacent surfaces, termed a hydroflotation effect.

Project coordinator diZerega and several contributors have reported the results of a large study in an article entitled "Reduction of Post-operative Pelvic Adhesions with Intraperitoneal 32% Dextran 70: A Prospective, Randomized Clinical Trial" in *Fertility and Sterility*, volume 40, number 5, for November 1983, pages 612–619. The authors, at page 618, indicate that the use of Dextran intraperitoneally has limitations such as the reported tendency of HYSKON to support bacterial proliferation and concern over the anaphylactoid potential of dextran. In addition, the benefit of Dextran 70 in preventing post-operative adhesions was shown to be limited to the more dependent regions of the pelvis. In U.S. Pat. No. 4,889,722 Sheffield and di Zerega disclose the use of tissue plasminogen activator in the inhibition of post-surgical adhesions.

Borten, Seibert, and Taymor in *Obstetrics and Gynecology*, volume 61, number 6, June 1983, pages 755–757 report in an article entitled "Recurrent Anaphylactic Reaction to Intraperitoneal Dextran 75 Used for Prevention of Postsurgical Adhesions". These authors indicate that anaphylactic reaction to Dextran administered intravenously is well documented and report such a reaction after intraperitoneal administration of Dextran.

Linsky in *The Journal of Reproductive Medicine* for Jan. 1987, pages 17–20 in an article entitled "Adhesion Reduction in the Rabbit Uterine Horn Model Using an Absorbable Barrier, TC-7". These authors report that the use of a resorbable fabric barrier provides a significant reduction in post-operative adhesion formation and that no gross remnants of the fabric barrier material were noted, subsequent to initial placement, after a two week period.

Oelsner et al in *The Journal of Reproductive Medicine* for Nov. 1987, volume 32, number 11, pages 812–814, report results of a comparison of sodium carboxylmethyl cellulose, 32% dextran 70, and condroitin sulfate to prevent the formation of postoperative adhesions in the rabbit uterus. The authors report superior results with chondroitin sulfate which is described as a member of a family of biochemical compounds referred to as glycosaminoglycans (formerly termed mucopolysaccharides), to which hyaluronic acid, heparitin sulfate and heparin also belong.

Peterson et al in *The Journal of Hand Surgery* for Jan. 1990, volume 15A, number 1, pages 48–56 state on page 48 that despite refinements in surgical technique and improved postoperative rehabilitation programs, results (of repair of lacerated flexor tendons) are often unsatisfactory because of the formation of adhesions around the repair site which restrict tendon gliding and prevent flexion of the digit. The authors on page 49 refer to use of biological barriers including paratenon, endothelial vein grafts, arteriol grafts, fascial sheath grafts, and synthetic materials such as, metal tubes, cellophane, celloidin, polytef (Teflon), polyethylene, millipore cellulose tubes, and silcone sheeting. Complications from use of these materials included severe inflammatory response, ingrowth of adhesions around the edges of the material, and prevention of nutrient diffusion leading to tendon necrosis. They conclude that a suitable biologic or synthetic flexor sheath patch has not yet gained widespread clinical acceptance. The authors tested primary tendon sheath repair, autogenous fascia lata patches, and a synthetic patch of expanded polytetraflorethylene surgical membranes. They concluded on p. 55 that restoration of the sheath integrity was beneficial in reducing adhesion formation, but it is not possible to advocate one particular method.

The use of ethylene oxide/propylene oxide block copolymers as surfactants for use in surgical scrub solutions and the topical application of 10% solutions of these copolymers to wounds is described in Edlich et al in the *Journal of Surgical Research*, volume 14, number 4, Apr. 1973, pages 277–284. The test results indicate that the copolymers having an ethylene oxide:propylene oxide ratio of 4:1 provide less inflammatory response in a wound to which the copolymer is applied in comparison with a copolymer having an ethylene oxide:propylene oxide ratio of 1:4. There is no indication in Edlich et al or any cited prior art that such copolymers are useful in reducing post-operative adhesions or that isotonic, aqueous solutions of such copolymers are useful in reducing post operative adhesions.

Over the years, methods have been developed to achieve the efficient delivery of a therapeutic drug to a mammalian body part requiring pharmaceutical treatment. Use of an aqueous liquid which can be applied at room temperature as a liquid but which forms a semi-solid gel when warmed to body temperature has been utilized as a vehicle for drug delivery since such a system combines ease of application with greater retention at the site requiring treatment than would be the case if the aqueous composition were not converted to a gel as it is warmed to mammalian body temperature. In U.S. Pat. No. 4,188,373, PLURONIC ® polyols are used in aqueous compositions to provide thermally gelling aqueous systems. Adjusting the concentration of the polymer provides the desired sol-gel transition temperature, that is, the lower the concentration of polymer, the higher the sol-gel transition temperature.

In U.S. Pat. Nos. 4,474,751; '752; '753; and 4,478,822 drug delivery systems are described which utilize thermosetting polyoxyalkylene gels; the unique feature of these systems is that both the gel transition temperature and/or the rigidity of the gel can be modified by adjustment of the pH and/or the ionic strength, as well as by the concentration of the polymer.

Other patents disclosing pharmaceutical compositions which rely upon an aqueous gel composition as a vehicle for the application of the drug or cosmetic preparation are U.S. Pat. Nos. 4,883,660; 4,861,760; 4,810,503; 4,767,619; 4,511,563; and 4,889,722.

Ionic polysaccharides have been used in the application of drugs by controlled release. Such ionic polysaccharides as chitosan or sodium alginate are disclosed as useful in providing spherical agglomerates of water-insoluble drugs in the *Journal of Pharmaceutical Sciences* volume 78, number 11, Nov. 1989, Bodmeier et al. Alginates have also been used as a depot substance in active immunization, as disclosed in the *Journal of Pathology and Bacteriology* volume 77, (1959), C. R. Amies. Calcium alginate gel formulations have also found use as a matrix material for the controlled release of herbicides, as disclosed in the *Journal of Controlled Release*, 3 (1986) pages 229–233, Pfister et al.

In U.S. Pat. No. 3,640,741, a molded plastic mass composed of the reaction product of a hydrophilic colloid and a cross-linking agent such as a liquid polyol, also containing an organic liquid medium such as glycerin, is disclosed as useful in the controlled release of medication or other additives. The hydrophilic colloid can be carboxymethyl cellulose gum or a natural alginate gum which is cross-linked with a polyol. The cross-linking reaction is accelerated in the presence of aluminum and calcium salts.

In U.S. Pat. No. 4,895,724, compositions are disclosed for the controlled release of pharmacological macromolecular compounds contained in a matrix of chitosan. Chitosan can be cross-linked utilizing aldehydes, epichlorohydrin, benzoquinone, etc.

In U.S. Pat. No. 4,795,642, there are disclosed gelatin-encapsulated, controlled-release compositions for release of pharmaceutical compositions, wherein the gelatin encloses a solid matrix formed by the cation-assisted gellation of a liquid filling composition incorporating a vegetable gum together with a pharmaceutically-active compound. The vegetable gums are disclosed as polysaccharide gums such as alginates which can be gelled utilizing a cationic gelling agent such as an alkaline earth metal cation.

While the prior art is silent with respect to the use of aqueous drug delivery vehicles which are isotonic to mammalian bodily fluids, osmotic drug delivery systems are disclosed in U.S. Pat. No. 4,439,196 which utilize a multi-chamber compartment for holding osmotic agents, adjuvants, enzymes, drugs, pro-drugs, pesticides, and the like. These materials are enclosed by semipermeable membranes so as to allow the fluids within the chambers to diffuse into the environment into which the osmotic drug delivery system is in contact. The drug delivery device can be sized for oral ingestion, implantation, rectal, vaginal, or ocular insertion for delivery of a drug or other beneficial substance. Since this drug delivery device relies on the permeability of the semipermeable membranes to control the rate of delivery of the drug, the drugs or other pharmaceutical preparations, by definition, are not isotonic with mammalian blood.

SUMMARY OF THE INVENTION

Polyoxyalkylene gel compositions, which can be rendered thermally-irreversible and processes are disclosed for reducing post-surgical adhesion formation/reformation in mammals following injury to the organs of the peritoneal, pelvic or pleural cavity. The compositions of the invention which can be applied at a desired pH and osmolality, are also useful to reduce adhesion formation/reformation in other body spaces such as the subdural, extraocular, intraocular, otic, synovial, tendon sheath, or those body spaces created either surgically or accidentally.

Compositions comprising at least one ionic polysaccharide and at least one polymer capable of forming an aqueous gel are useful. The useful compositions comprise (1) a combination of a polyether, an ionic polysaccharide and a surfactant or (2) a polyoxyalkylene block copolymer and an ionic polysaccharide. Polyphase systems are also useful and may contain non-aqueous solutes, non-aqueous solvents, and other non-aqueous additives. Homogeneous, polyphase systems can contain such additives as water insoluble high molecular weight fatty acids and alcohols, fixed oils, volatile oils and waxes, mono-, di-, and triglycerides, and synthetic, water insoluble polymers without altering the functionality of the system.

In a preferred embodiment of the invention, the concentration of the block copolymer in the compositions of the invention can be adjusted to take advantage of the thermally reversible gellation properties of certain polyoxyalkylene block copolymers. For instance, at certain concentrations aqueous solutions of said block copolymers form clear gels at mammalian body temperatures but are liquids at ambient temperatures. The aqueous solutions of said block copolymers can be provided as isotonic and pH balanced compositions which match the pH and osmotic pressure of mammalian bodily fluids. Subsequent to deposition of the compositions of the invention in the peritoneal, pelvic, or pleural cavity of a mammal, or other body spaces, as described above, the polyoxyalkylene block copolymer and ionic polysaccharide mixture can be rendered thermally-irreversible (1) by contact with bodily fluids which can supply a counter-ion, such as calcium, or (2) by contact with a counter-ion supplied in latent form as a component of the mixture. The thermally-irreversible gelled mixture is subsequently absorbed by the tissues with which it is in contact and the block copolymer is eventually excreted in a non-metabolized form, mainly in the urine.

In another embodiment of the invention, aqueous gels are produced by combination of an alpha-olefin epoxide capped polyether and a surfactant, as described in U.S. Pat. No. 4,810,503. In this embodiment, the aqueous gels are applied in admixture with an ionic polysaccharide, as gels to injured tissues in the peritoneal, pelvic, or plural cavities or other body spaces to reduce post-surgical adhesion formation/reformation. These gels are usefully stiffened upon contact with a suitable counter-ion.

In addition to functioning as a means of reducing post-operative adhesion formation/reformation in mammals following surgical or accidental injury to the peritoneal pelvic or pleural cavity or other body spaces, the inventive mixtures, which comprise a polyoxyalkylene and an ionic polysaccharide, can be formulated to provide a desired osmolality including an isotonic mixture useful in surrounding the surgical injury. For instance, the aqueous mixtures comprising a polyoxyalkylene block copolymer and ionic polysaccharide can be instilled within the uterine cavity as a distending medium during diagnostic or operative intrauterine endoscopic procedures. This procedure has two advantages. First, since certain aqueous concentrations of the preferred polyoxyalkylene block polymers form a clear gel at mammalian body temperature, their use is well suited for visualization of the uterine cavity. Second, since these aqueous solutions, in one embodiment, are liquids at room temperature and below and form a clear gel at mammalian body temperature, the use of said solutions to separate the uterine cavity walls will diminish or prevent post-surgical adhesion formation. Similarly, the application of the aqueous, capped, polyoxyalkylene, polyether-surfactant combination as gels, in another embodiment, provides a similar adhesion reducing effect.

The compositions of the invention comprise aqueous mixtures of a polyoxyalkylene polymer and an ionic polysaccharide, and, optionally, a latent counter-ion useful to gel (cross-link) the polysaccharide upon release of or contact with the counter-ion. The aqueous mixture can be applied, in one embodiment, to mammalian body spaces as a low viscosity liquid at ambient temperatures which, upon contact with the mammalian body, forms a semi-solid gel having a very high viscosity. The optional counter-ion can be released to render the gel thermally-irreversible. Where the compositions do not include a counter-ion, thermally-irreversible gellation of the mixture of the ionic polysaccharide and polyoxyalkylene polymer is achieved by contact with calcium or other suitable counter-ions present in bodily fluids.

The compositions of the invention comprising an ionic polysaccharide and a polyoxyalkylene block copolymer or said ionic polysaccharide and capped polyether-surfactant gels can be utilized optionally in combination with a humectant or bacteriostatic and bactericidal agents, fibrinolytic agents, and agents effective in preventing leucocyte migration into the area of surgical injury.

The preferred ionic polysaccharides are polymers such as chitosan or alginates. Aqueous solutions of these alginate ionic polysaccharides form gels upon contact with alkaline earth metal counter-ions, preferably, calcium, strontium and aluminum. Metal tripolyphosphates can be used to gel aqueous solutions of chitosan ionic polysaccharides.

DESCRIPTION OF THE DRAWING

The drawing provides a curve showing the penetration as measured by a gravity drop penetrometer of a 20 mm thickness aqueous gel of Poloxamer 407 and an alginate prepared in accordance with the procedure of Example 1. The scale at the left side of the plot indicates the depth of penetration, while the scale on the right side of the plot indicates the temperature of the composition when tested. The arrow on the plot indicates the point at which an aqueous solution of calcium ions at a concentration of 0.137 molar is made to contact the gelled poloxamer 407 and alginate so as to cross-link the polysaccharide component of the mixture.

DETAILED DESCRIPTION OF THE INVENTION

It has been found that aqueous pharmaceutical vehicles containing a polyoxyalkylene block copolymer, which have the unique feature of being liquid at ambient temperatures and transitioning at mammalian body temperatures to a semi-solid gel, can be thermally-irreversibly gelled and made resistant to shear thinning, as well as more resistant to penetration by the inclusion of an ionic polysaccharide in admixture with the polyoxyalkylene polymer. Contacting the ionic polysaccharide with counter-ion gels (cross-links) the polysaccharide and renders the mixture a thermally-irreversible gel.

A process and compositions are disclosed for reducing post-operative adhesion formation/reformation in mammals following surgical or accidental injury to the organs of the peritoneal or pleural cavity or other body spaces. In this specification and claims, the terms "peritoneal" and "abdominal" cavity are used as synonyms, as are the terms "pleural" and "thoracic" cavity. The compositions can include at least one of a bacteriostatic or bactericidal agent, an agent effective in preventing leucocyte migration into the area of surgical injury, and a fibrinolytic agent.

In one embodiment of the invention, the preferred aqueous, polyoxyalkylene block copolymer compositions including an ionic polysaccharide are prepared at concentrations so as to take advantage of the gelation properties of certain of said block copolymers and at a desired pH and desired osmotic pressure, preferably, that which matches that of bodily fluids (pH 7.4 and 290 mOsm/kg). When certain of the polyoxyalkylene block copolymers of the invention are present in aqueous solutions at concentrations, preferably, of about 15% to about 30% by weight, such compositions can provide liquid compositions at ambient temperatures or below which revert to gel compositions upon contact with living mammalian tissue.

Alternatively, useful compositions of the invention include (1) aqueous compositions comprising at least one ionic polysaccharide, at least one polyoxyalkylene block copolymer, which does not form gels at mammalian body temperature, as well as (2) aqueous, polyoxyalkylene gel polymers comprising at least one ionic polysaccharide, an alpha olefin epoxide capped polyether and a surfactant. These compositions also include, optionally, a counter-ion and, optionally, at least one adjuvant such as a humectant, a bactericide, a bacteriostatic agent, an antihistamine, or a decongestant, an agent to prevent leucocyte migration into the area of surgical injury, or a fibrinolytic agent. The compositions comprising a polyether and a surfactant are applied to injured tissue in a major amount in combination with a minor amount of optional counter-ion and adjuvant. It is believed that the aqueous compositions of the invention which do not form gels upon contact with living mammalian tissue as well as those which are applied to mammalian tissue in the gel state, also function to prevent the formation/reformation of adhesions subsequent to surgical injury by a mechanism of action which has been termed in the prior art "hydroflotation". Thus the injured tissues are prevented from contacting adjacent tissues by the means of the inclusion of a foreign fluid or gel in the peritoneal, pelvic, or pleural cavity or other body spaces. It is believed that the mechanism of action to prevent the formation/reformation of adhesions is, in addition to hydroflotation, properly characterized as the result of separating the adjacent mammalian tissues by a firm, adherent gel coating.

The polyoxyalkylene block copolymer compositions of one embodiment of the invention include a mixture of at least one block copolymer as below defined, at least one ionic polysaccharide, optionally, a counter-ion and, optionally, at least one of an adjuvant such as a humectant, a bactericide, a bacteriostatic agent, an antihistamine, or a decongestant, an agent to prevent leucocyte migration into the area of surgical injury, or a fibrinolytic agent. The copolymer and ionic polysaccharide are applied to injured tissue in a major amount in combination with a minor amount of optional counter-ion and adjuvant.

In general, the compositions of the present invention will contain from about 0.01% to about 60% by weight of the medicament or pharmaceutical, from about 10 to about 50% by weight of the polyoxyalkylene polymer, about 0.2 to about 2.5% by weight, preferably, about 0.5 to about 1.5% by weight of ionic polysaccharide, and from 80% to about 20% by weight of water. In special situations, however, the amounts may be varied to increase or decrease the dosage schedule.

Useful humectants include, but are not limited to glycerin, propylene glycol, and sorbitol. Useful bactericides which can be administered in admixture with the aqueous compositions of the invention include antibacterial substances such as B-lactam antibiotics, such as cefoxitin, n-formamidoyl thienamycin and other thienamycin derivatives, tetracyclines, chloramphenicol, neomycin, gramicidin, bacitracin, sulfonamides; aminoglycoside antibiotics such as gentamycin, kanamycin, amikacin, sisomicin and tobramycin; nalidixic acids and analogs such as norfloxacin and the antimicrobial combination of fluoroalanine/pentizidone; nitrofurazones, and the like. Antihistaminics and decongestants such as pyrilamine, chlorpheniramine, tetrahydrazoline, antazoline, and the like, can also be used in admixtures as well as anti-inflammatories such as cortisone, hydrocortisone, beta-methasone, dexamethasone, fluocortolone, prednisolone, triamcinolone, indomethacin, sulindac, its salts and its corresponding sulfide, and the like.

If desired, the compositions of the invention may also contain preservatives, co-solvents, suspending agents, viscosity enhancing agents, ionic strength and osmolality adjusters and other excipients in addition to the medicament and buffering agents. Suitable water soluble preservatives which may be employed in the drug delivery vehicle are sodium bisulfite, sodium thiosulfate, ascorbate, benzalkonium chloride, chlorabutanol, thimerosal, phenylmercuric borate, parabens, benzyl alcohol, phenyl ethanol, and others. These agents may be present, generally, in amounts of about 0.001% to about 5% by weight and, preferably, in the amount of about 0.01 to about 2% by weight.

Suitable water soluble buffering agents are alkali or alkaline earth metal carbonates, phosphates, bicarbonates, citrates, borates, acetates, succinates, and the like, such as sodium phosphate, citrate, borate, acetate, bicarbonate, carbonate, and tromethamine (TRIS). These agents are present in amounts sufficient to maintain a desired pH. Preferably, the system is buffered to pH 7.4±0.2 and, most preferably, pH 7.4. The buffering agent can comprise as much as 5%, on a weight basis, of the total composition. Representative preservatives are sodium bisulfite, sodium thiosulfate, ascorbate, benzalkonium chloride, chlorobutanol, thimerosal, phenylmercuric borate, parabens, benzylalcohol and phenylethanol.

Useful leucocyte migration preventing agents which can be used in the inventive mixtures include, but are not limited to, silver sulfadiazine, acetylsalicylic acid, indomethacin, and Nafazatrom. Useful fibrinolytic agents include urokinase, streptokinase, tissue plasminogen activator (TPA), and acylated plasmin.

The block copolymer compositions of the invention comprise at least one polyoxyalkylene block copolymer of the formula:

$$Y[(A)_n-E-H]_x \qquad (I)$$

wherein A is a polyoxyalkylene moiety having an oxygen/carbon atom ratio of less than 0.5, x is at least 2, Y is derived from water or an organic compound containing x reactive hydrogen atoms, E is a polyoxyalkylene moiety constituting at least about 60% by weight of the copolymer, n has a value such that the average molecular weight of A is at least about 500 to about 900, as determined by the hydroxyl number of a hydrophobe base intermediate, $$Y[(A)_n-H]_x \qquad (II)$$

and the total average molecular weight of the copolymer is at least about 5000.

Generally, copolymers useful in the compositions of the invention are prepared by first condensing 1,2 butylene oxide with a water soluble organic compound initiator containing 1 to about 6 carbon atoms, such as, 1,4 butylene glycol or propylene glycol and at least 2 reactive hydrogen atoms to prepare a polyoxyalkylene polymer hydrophobe of at least about 500, preferably, at least about 1000, most preferably, at least about 1500 average molecular weight. Subsequently, the hydrophobe is capped with an ethylene oxide residue. Specific methods for preparing these compounds are described in U.S Pat. No. 2,828,345 and British Patent No. 722,746, both of which are hereby incorporated by reference.

Useful polyoxybutylene based block copolymers conform to the following generic formula:

$$HO(C_2H_4O)_b(C_4H_8O)_a(C_2H_4O)_bH \qquad (III)$$

wherein a and b are integers such that the hydrophobe base represented by ($C_4H_8O$) has a molecular weight of at least about 500, preferably, at least about 1000 and most preferably, at least about 3000, as determined by hydroxyl number, the polyoxyethylene chain constituting at least about 60%, preferably, at least about 70% by weight of the copolymer and the copolymer having a total average molecular weight of at least about 5000, preferably, at least about 10,000, and, most preferably, at least about 15,000.

The copolymer is characterized in that all the hydrophobic oxybutylene groups are present in chains bonded to an organic radical at the former site of a reactive hydrogen atom thereby constituting a polyoxybutylene base copolymer. The hydrophilic oxyethylene groups are used to cap the polyoxybutylene base polymer.

Polyoxyethylene-polyoxypropylene block copolymers which can be used to form aqueous gels can be represented by the following formula:

$$HO(C_2H_4O)_b(C_3H_6O)_a(C_2H_4O)_bH \qquad (IV)$$

wherein a and b are integers such that the hydrophobe base represented by ($C_3H_6O$) has a molecular weight of at least about 900, preferably, at least about 2500, most preferably, at least about 4000 average molecular weight, as determined by hydroxyl number; the polyoxyethylene chain constituting at least about 60%, preferably, at least about 70% by weight of the copolymer and the copolymer having a total average molecular weight of at least about 5000, preferably, at least about 10,000, and most preferably, at least about 15,000.

Polyoxyethylene-polyoxypropylene block copolymer adducts of ethylene diamine which can be used may be represented by the following formula:

(V)

wherein a and b are integers such that the copolymer may have (1) a hydrophobe base molecular weight of at least about 2000, preferably, at least about 3000, and most preferably, at least about 4500, (2) a hydrophile content of at least about 60%, preferably, at least about 70% by weight, and (3) a total average molecular weight of at least about 5000, preferably, at least about 10,000, and most preferably, at least about 15,000.

The hydrophobe base of the copolymer of formula V is prepared by adding propylene oxide for reaction at the site of the four reactive hydrogen atoms on the amine groups of ethylene diamine. An ethylene oxide residue is used to cap the hydrophobe base. The hydrophile polyoxyethylene groups are controlled so as to constitute at least about 60%, preferably, at least about 70% by weight, and most preferably, at least about 80% by weight of the copolymer.

The procedure used to prepare aqueous solutions which form gels of the polyoxyalkylene block copolymers is well known. Either a hot or cold process for forming the solutions can be used. A cold technique involves the steps of dissolving the polyoxyalkylene block copolymer at a temperature of about 5° to about 10° C. in water. When solution is complete the system is brought to room temperature whereupon it forms a gel. If the hot process of forming the gel is used the polymer is added to water heated to a temperature of about 75° C. to about 85° C. with slow stirring until a clear homogenous solution is obtained. Upon cooling, a clear gel is formed. Block copolymer gels containing polyoxybutylene hydrophobes must be prepared by the above hot process, since these will not liquify at low temperatures.

As used herein, the term "gel" is defined as a solid or semisolid colloid containing a certain quantity of water. The colloidal solution with water is often called a "hydrosol".

The organic compound initiator which is utilized in the process for the preparation of the polyoxyalkylene block copolymers generally is water or an organic compound and can contain a plurality of reactive hydrogen atoms. Preferably, Y in formulas I and II above is defined as derived from a water soluble organic compound having 1 to about 6 carbon atoms and containing x reactive hydrogen atoms where x has a value generally, of at least 1, preferably, a value of at least 2. Falling within the scope of the compounds from which Y is derived from water soluble organic compounds having at least two reactive hydrogen atoms are water soluble organic compounds such as propylene glycol, glycerin, pentaerythritol, trimethylolpropane, ethylene diamine, and mixtures thereof and the like.

The oxypropylene chains can optionally contain small amounts of at least one of oxyethylene or oxybutylene groups. Oxyethylene chains can optionally contain small amounts of at least one of oxypropylene or oxybutylene groups. Oxybutylene chains can optionally contain small amounts of at least one of oxyethylene or oxypropylene groups. The physical form of the polyoxyalkylene block copolymers can be a viscous liquid, a paste, or a solid granular material depending upon the molecular weight of the polymer. Useful polyoxyalkylene block copolymers generally have a total average molecular weight of about 5,000 to about 50,000, preferably, about 5,000 to about 35,000 and most preferably, about 10,000 to about 25,000.

In addition to those polyoxyalkylene polymers described above, which are suitable in the formation of the pharmaceutical compositions of the invention, other polyoxyalkylene polymers which form gels at low concentrations in water are suitable. These are described in U.S. Pat. No. 4,810,503, incorporated herein by reference. These polymers are prepared by capping conventional polyoxyalkylene polyether polyols with an alpha-olefin epoxide having an average of about 20 to about 45 carbon atoms, or mixtures thereof. Aqueous solutions of these polymers gel in combination with surfactants, which can be ionic or nonionic. The combination of the capped polyether polymers and the surfactants provide aqueous gels at low concentrations of the capped polymer and surfactant which generally do not exceed 10% by weight total. Detailed methods of preparing these aqueous gels are disclosed in U.S. Pat. No. 4,810,503. Preparation of said aqueous gels is generally described below. Preferred surfactants for use in preparing these gels are also disclosed in said patent.

A conventional copolymer polyether polyol is prepared by preparing block or heteric intermediate polymers of ethylene oxide and at least one lower alkylene oxide having 3 to 4 carbon atoms as intermediates. These are then capped with the alpha-olefin epoxide to prepare the polymers of this invention. Ethylene oxide homopolymers capped with said alpha-olefin oxides are also useful as intermediates.

The heteric copolymer intermediate is prepared by mixing ethylene oxide and at least one lower alkylene oxide having 3 to 4 carbon atoms with a low molecular weight active hydrogen-containing compound initiator having at least two active hydrogens and preferably, 2 to 6 active hydrogen atoms such as a polyhydric alcohol, containing from 2 to 10 carbon atoms and from 2 to 6 hydroxyl groups, heating said mixture to a temperature in the range of about 50° C. to 150° C., preferably, from 80° C. to 130°., under an inert gas pressure, preferably, from about 30 psig to 90 psig.

A block copolymer intermediate is prepared by reacting either the ethylene oxide or said alkylene oxide having 3 to 4 carbon atoms with said active hydrogen-containing compound followed by reaction with the other alkylene oxide.

The ethylene oxide and the alkylene oxides having from 3 to 4 carbon atoms are used in said intermediates in amounts so that the resulting polyether product will contain at least 10 percent by weight, preferably about 70 percent to about 90 percent by weight, ethylene oxide residue. The ethylene oxide homopolymer intermediate is prepared by reacting ethylene oxide with said active hydrogen-containing compound. The reaction conditions for preparing the block copolymer and ethylene oxide homopolymer intermediates are similar to those for the heteric copolymer intermediate. The temperature and pressure are maintained in the above ranges for a period of about one hour to ten hours, preferably one to three hours.

The alpha-olefin oxides which are utilized to modify the conventional polyether intermediate of the prior art are those oxides and the commercially available mixtures thereof generally containing an average of about 20 to 45, preferably about 20 to 30, carbon atoms. The amount of alpha-olefin required to obtain the more efficient capped polyethers is generally about 0.3 to 10 percent, preferably about 4 to 8 percent, of the total weight of the polyethers of the invention.

Since the preparation of heteric and block copolymers of alkylene oxides and ethylene oxide homopolymers are well known in the art, further description of the preparation of said polymers is unnecessary. Further details of the preparation of heteric copolymers of lower alkylene oxide can be obtained in U.S. Pat. No. 3,829,506, incorporated herein by reference. Further information on the preparation of block copolymers of lower alkylene oxides can be obtained in U.S. Pat Nos. 3,535,307; 3,036,118; 2,979,578; 2,677,700; and 2,675,619 incorporated herein by reference.

The surfactants may be ionic or non-ionic and many surfactants and types of surfactants may be employed. While all surfactants may not be effective in the preparation of the isotonic gels of the instant invention, the fact that many are effective makes it a simple matter for one skilled in the art to select such surfactant with a minimum of trial and error.

The amounts of capped polyether polymer and surfactant may be as little as 1.0 percent by weight or less of each depending on the type and amount of the other component. There appears to be no maximum amount of either component other than that dictated by economic considerations. However, the total amount of capped polymer and surfactant generally does not exceed 10 percent by weight.

The ionic polysaccharides found useful in the present invention are hydrophilic colloidal materials and include the natural gums, i.e., the ammonium and alkali metal salts of alginic acid and mixtures thereof as well as chitosan, which is a common name for the deacetylated form of chitin. Chitin is a natural product comprising poly- (N-acetyl-D-glucosamine). The alginates can be any of the water-soluble alginates including the alkali metal (sodium, potassium, lithium, rubidium and cesium) salts of alginic acid, as well as the ammonium salt, and the soluble alginates of an organic base such as mono-, di-, or tri-ethanolamine, aniline and alike.

Generally, aqueous solutions of chitosan can be gelled (cross-linked) with multivalent anion gelling agents. These preferably comprise water soluble metal or ammonium phosphates or polyphosphates such as an alkali metal or ammonium phosphate, tripolyphosphate, pyrophosphate, or metaphosphate. Generally, a molar ratio of counter-ion to chitosan or alginate ionic polysaccharide of about 1:1 to about 10:1, preferably, about 2:1 to about 5:1, and, most preferably, about 3:1 to about 5:1 is used to render the compositions of the invention thermally-irreversibly gelled.

Generally, the useful counter-ions for rendering thermally irreversible the alginate ionic polysaccharide in combination with the polyoxyalkylene polymer compositions of the invention are cationic gelling agents, preferably, comprising an alkaline earth metal, or aluminum counter-ions. Other cationic gelling agents include divalent copper, cadmium, cobalt, nickel, zinc, manganese, and iron cations. Trivalent cation gelling agents include aluminum, chromium, and trivalent iron. The most preferred counter-ions for gelling the alginate ionic polysaccharide are contained in ionic compounds selected from pharmaceutically-acceptable flourides, citrates, phosphates, tartrates, sulfates, acetates, borates, chlorides, and the like having cations such as strontium, calcium, and aluminum. Especially preferred are counter-ions obtained from inorganic salts such as the chloride salts, such as strontium chloride, calcium chloride, and mixtures thereof.

While the counter ion, such as calcium, may be obtained from bodily fluids, it is preferred that the counter-ion be present in latent form in the alginate ionic polysaccharide and polyoxyalkalene polymer compositions of the invention. Alternatively, a two part system can be used in which the counter-ion is topically applied to the aqueous polymer and ionic polysaccharide components of the mixture subsequent to their topical application to a body space. It is most preferred to incorporate the counter-ion in a latent form together with the ionic polysaccharide and polyoxyalkylene polymer compositions of the invention. This may be accomplished by either encapsulating an aqueous solution of one of the cationic gelling agents, previously described above, or by the incorporation of the cationic gelling agent with an ion exchange resin or incorporation of the cationic gelling agent into a matrix which provides for the controlled, slow-release of the gelling agent. For instance, the gelatin-encapsulated controlled-release compositions disclosed in U.S. Pat. No. 4,795,642, incorporated herein by reference, disclose the preparation of a gelatin shell encapsulating a controlled-release formulation in which the gelatin composition includes calcium chloride and a gelling agent. Alternatively, the counter-ion can be incorporated as an aqueous solution of a cationic gelling agent encapsulated in a vehicle composed, for instance, of alpha-tocopherol, as disclosed in U.S. Pat. No. 4,861,580, incorporated herein by reference. The counter-ion can be microencapsulated in a bodily heat sensitive medium. For instance, the walls of the microcapsule can be made of mono-, di-, or tri-glycerides or other natural or synthetic heat sensitive polymer medium. Alternatively, ion exchange resins can be used to incorporate the desired counter-ions of the invention and to release the desired counter-ion upon contact with an environment opposite in pH to the pH of the ion exchange resin.

Post-operative pelvic adhesions have been associated with infertility. Significant periadnexal adhesions have been found, as reported by Musich and Behrman, as previously cited, upon laparoscopy in 72% of 106 patients having unexplained infertility who had previously undergone various pelvic surgical procedures. Prevention of such adhesions has been proposed in the prior art by treatment with aqueous dextran solutions of low molecular weight. The prior art use of aqueous dextran solutions (i.e., dextran 70 at 32% solids) has shown adverse reactions and little or no reduction of post-operative pelvic adhesions.

In addition, an oxidized cellulose fabric barrier (sold under the trade designation TC-7 by Johnson and Johnson Products, Inc., New Brunswick, N.J.), which is resorbable subsequent to utilization, has been used in the prior art as a treatment to prevent adhesions to the peritoneum by preventing abutting injured organ surfaces from making contact therewith. Chondroitin sulfate solutions have also been proposed in the prior art for intraperitoneal use in the prevention of adhesions in rabbits. Each of these proposed prior art methods of avoiding post-operative adhesions have disadvantages which are overcome by the method of the present invention.

The mechanism of action of all of these prior art treatments is proposed to be the result of the persistent separation of adjacent surgically injured surfaces thus permitting healing to occur without the formation of fibrinous bands between abutting surfaces which are characterized as adhesions. For instance, upon injury to the peritoneum there results an outpouring of a serosanguinous exudate which is of a proteinaceous nature. This fluid subsequently coagulates, producing fibrinous bands between abutting surfaces that become subsequently organized by fibroblast proliferation to produce collagenous adhesions. This process is thought to be initiated and well advanced within the first three days subsequent to surgical injury.

Preferably, the block copolymers which are useful are selected from those defined above in formula I which contain at least about 60% by weight, preferably at least about 70%, by weight and most preferably at least about 80% by weight of the residue of ethylene oxide (polyoxyethylene moiety). Said copolymers have a total average molecular weight of at least about 5000, and form a gel at mammalian body temperature, when in an aqueous solution at a concentration generally, of about 10 to about 40%, preferably, about 15 to about 30% by weight and most preferably, about 18% to about 25% by weight.

The proportion of water used in the compositions of the invention is about 20% to about 80%, by weight, preferably, about 30% to about 70%, by weight, and most preferably, about 35% to about 65% by weight, based upon the total weight of the compositions of the invention. Generally, a molar ratio of counter-ion to chitosan or alginate of about 1:1 to about 10:1, preferably, about 2:1 to about 5:1, and, most preferably, about 3:1 to about 5:1 is used to render the compositions of the invention thermally-irreversibly gelled.

Useful polyoxyalkylene block copolymers which will form gels in such aqueous solutions can be prepared using a hydrophobe base (such as A in Formulas I and II) derived from propylene oxide, butylene oxide, or mixtures thereof. These block copolymers and representative methods of preparation are further generally described in U.S. Pat. Nos. 2,677,700; 2,674,619; and U.S. Pat. No. 2,979,528, incorporated herein by reference.

Generally, the polyoxybutylene-based block copolymers useful in the compositions of the invention are prepared by first condensing 1,2 butylene oxide with a water soluble organic compound initiator containing 1 to about 6 carbon atoms such as 1,4 butylene glycol or propylene glycol and at least 2 reactive hydrogen atoms to prepare a polyoxyalkylene polymer hydrophobe of at least about 500, preferably at least about 1000, and most preferably, at least about 1500 average molecular weight. Subsequently, the hydrophobe is capped with an ethylene oxide residue. Specific methods for preparing these compounds are described in U.S. Pat. No. 2,828,345 and British Patent No. 722,746, both of which are hereby incorporated by reference.

Useful polyoxybutylene based block copolymers conform to the following generic formula:

$$HO(C_2H_4O)_b(C_4H_8O)_a(C_2H_4O)_bH \qquad (III)$$

wherein a and b are integers such that the hydrophobe base represented by ($C_4H_8O$) has a molecular weight of at least about 500, preferably, at least about 1000 and, most preferably, at least about 3000, as determined by hydroxyl number, the polyoxyethylene chain constituting at least about 60%, preferably, at least about 70% by weight of the copolymer, and the copolymer having a total average molecular weight of at least about 5000, preferably, at least about 10,000, and, most preferably, at least about 15,000.

The copolymer is characterized in that all the hydrophobic oxybutylene groups are present in chains bonded to an organic radical at the former site of a reactive hydrogen atom thereby constituting a polyoxybutylene base copolymer. The hydrophilic oxyethylene groups are used to cap the polyoxybutylene base polymer.

Polyoxyethylene-polyoxypropylene block copolymers which can be used to form aqueous gels can be represented by the following formula:

$$HO(C_2H_4O)_b(C_3H_6O)_a(C_2H_4O)_bH \qquad (IV)$$

wherein a and b are integers such that the hydrophobe base represented by ($C_3H_6O$) has a molecular weight of at least about 900, preferably, at least about 2500, most preferably, at least about 4000 average molecular weight, as determined by hydroxyl number; the polyoxyethylene chain constituting at least about 60%, preferably, at least about 70% by weight of the copolymer, and the copolymer having a total average molecular weight of at least about 5000, preferably, at least about 10,000, and most preferably, at least about 15,000.

Polyoxyethylene-polyoxypropylene block copolymer adducts of ethylene diamine which can be used may be represented by the following formula:

wherein a and b are integers such that the copolymer may have (1) a hydrophobe base molecular weight of at least about 2000, preferably, at least about 3000, and most preferably, at least about 4500, (2) a hydrophile content of at least about 60%, preferably, at least about 70% by weight, and (3) a total average molecular weight of at least about 5000, preferably, at least about 10,000, and most preferably, at least about 15,000.

The hydrophobe base of the copolymer of formula V is prepared by adding propylene oxide for reaction at the site of the four reactive hydrogen atoms on the amine groups of ethylene diamine. An ethylene oxide residue is used to cap the hydrophobe base. These hydrophile polyoxyethylene groups are controlled so as to constitute at least about 60%, preferably, at least about 70% by weight, and most preferably, at least about 80% by weight of the copolymer.

The procedure used to prepare aqueous solutions which form gels of the polyoxyalkylene block copolymers is well known. Either a hot or cold process for forming the solutions can be used. A cold technique involves the steps of dissolving the polyoxyalkylene block copolymer at a temperature of about 5° to about 10° C. in water. When solution is complete the system is brought to room temperature whereupon it forms a gel. If the hot process of forming the gel is used the polymer is added to water heated to a temperature of about 75° C. to about 85° C. with slow stirring until a clear homogenous solution is obtained. Upon cooling, a clear gel is formed. Block copolymer gels containing polyoxybutylene hydrophobes must be prepared by the above hot process, since these will not liquify at low temperatures. As used herein, the term "gel" is defined as a solid or semisolid colloid containing a certain quantity of water. The colloidal solution with water is often called a "hydrosol".

The organic compound initiator which is utilized in the process for the preparation of the polyoxyalkylene block copolymers, generally, is water or an organic compound and can contain a plurality of reactive hydrogen atoms. Preferably, Y in formulas I and II above is defined as derived from a water soluble organic compound having 1 to about 6 carbon atoms and containing x reactive hydrogen atoms where x has a value, generally, of at least 1, preferably, a value of at least 2. Falling within the scope of the compounds from which Y is derived from water soluble organic compounds having at least two reactive hydrogen atoms are water soluble organic compounds such as propylene glycol, glycerin, pentaerythritol, trimethylolpropane, ethylene diamine, and mixtures thereof and the like.

The oxypropylene chains can, optionally, contain small amounts of at least one of oxyethylene or oxybutylene groups. Oxyethylene chains can, optionally, contain small amounts of at least one of oxypropylene or oxybutylene groups. Oxybutylene chains can, optionally, contain small amounts of at least one of oxyethylene or oxypropylene groups. The physical form of the polyoxyalkylene block copolymers can be a viscous liquid, a paste, or a solid granular material depending upon the molecular weight of the polymer. Useful polyoxyalkylene block copolymers generally have a total average molecular weight of about 5000 to about 50,000, preferably, about 5,000 to about 35,000 and most preferably, about 10,000 to about 25,000.

Preferably, the polyoxyalkylene block copolymer is applied to surgically injured tissue as an aqueous solution which upon contact with living mammalian tissue forms a firm, adherent gel. Where a polyoxyalkylene block copolymer is a viscous liquid or paste, these compositions can be applied without dilution to areas of surgical injury in the abdominal or thoracic cavities.

The following examples illustrate the various aspects of the invention but are not intended to limit its scope. Where not otherwise specified throughout this specification and claims, temperatures are given in degrees centigrade, and parts, percentages, and proportions are by weight.

EXAMPLE 1

In this Example a formulation is described of a thermo-irreversible composition of the invention, also characterized as iso-osmotic, sterile, and having a pH of 7.4±0.2. An aqueous solution was made of a polyoxyethylene-polyoxypropylene block copolymer having the structure generically shown above as Formula IV and having a polyoxypropylene hydrophobe base average molecular weight of about 4000, a total average molecular weight of about 11,500, and containing oxyethylene groups in the amount of about 70% by weight of the total weight of copolymer. This copolymer is sold under the trademark PLURONIC® F-127 (also known as Poloxamer 407) by the BASF Corporation, Parsippany, N.J. A solution in TRIS hydrochloride buffer was made by dissolving said polymer and sodium alginate in cold (4° C.) buffer to give a concentration of 19% by weight and 1% by weight sodium alginate. More specific solution procedures are described in "Artificial Skin I Preparation and Properties of PLURONIC F-127 Gels For Treatment of Burns", *Journal of Biomedical Material Research* 6, 527, 1972, incorporated herein by reference. The block copolymer has the formula:

(VI)

Figure 1:
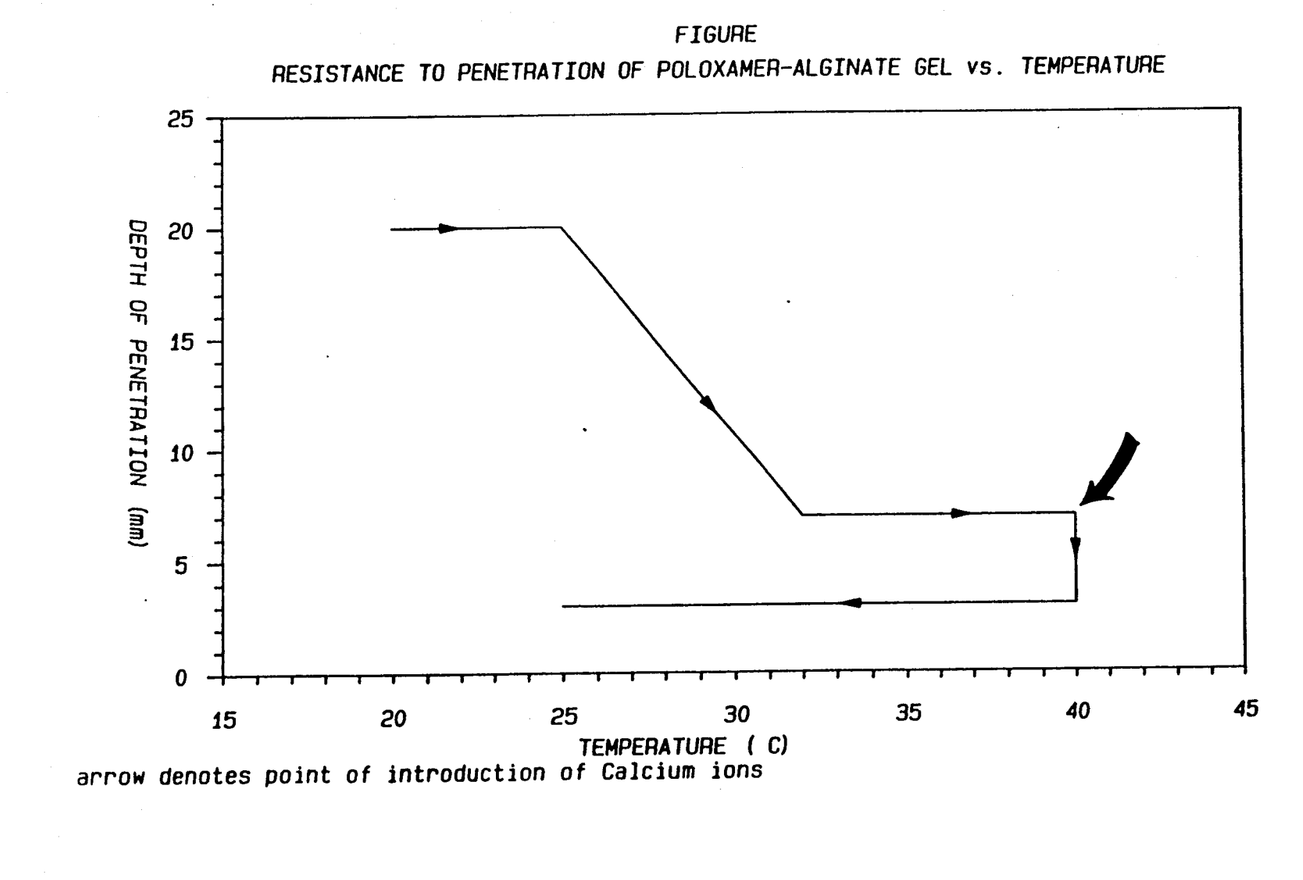

This formulation forms the basis for the FIGURE in which the curve shows the penetration of a 20 mm thickness aqueous gel at various temperatures. After contact of the gel with calcium ions, as indicated by the arrow at 40° C., the gel strength is not reduced or the composition rendered fluid by lowering the temperature to 25° C.

EXAMPLE 2

The composition of Example 1 is applied to the abdominal cavity of surgically injured, anesthetized rats. The composition of Example 1 is specifically applied to opposing injured areas of the abdominal cavity consisting of one of the uterine horns and the opposing portion of parietal peritoneum. These areas are previously excised prior to the application of the composition of Example 1. The other uterine horn is stripped of serosa and the opposing square centimeter of parietal peritoneum is excised but not treated with the composition of Example 1. The application of the composition of Example 1 is seen to initially form a thermo-reversible gel upon contact with the body tissues of the rats and subsequently, a second application of the composition of Example 1 is applied. The composition of Example 1 is subsequently rendered thermally-irreversible by contact with the bodily fluids of the rats. Thereafter, the treated portions of the uterine horn and the untreated portions of the uterine horn are attached within 0.5 centimeters of the surgical injury to the peritoneal parietal area by single 3-0 VICRYL ligature suture. This is done to insure that the injured surface of the uterine horn remains in close proximity to the surgical injury of the parietal area of the peritoneum until re-peritonealization occurs. The abdominal wall is closed with a single layer of interrupted 0—0 VICRYL suture and 21 days later, the rats are sacrificed and the abdomen examined for the presence of adhesions. It is noted that adhesions develop where surgically injured areas of the uterine horn and parietal peritoneum are left untreated, while adhesions fail to develop where the injured areas are treated with the composition of Example 1.

EXAMPLE 3

Example 1 is repeated substituting for Poloxamer 407, 2% by weight of polymer #2, as described in U.S. Pat. No. 4,810,503 and 4% by weight of surfactant #1, as described therein. The balance of the percentage of Poloxamer 407 used in Example 1 is made up with TRIS hydrochloride buffer. This composition forms a soft gel at room temperature which is usefully stiffened upon exposure (by topical application) to a 2% by weight aqueous solution of calcium chloride. Substantially similar pH and osmolality results are obtained.

EXAMPLE 4

The composition of Example 3 is applied to the abdominal cavity of surgically injured, anesthetized rats. The composition of Example 3 is specifically applied to opposing injured areas of the abdominal cavity consisting of one of the uterine horns and the opposing portion of parietal peritoneum. These areas are previously excised prior to the application of the composition of Example 3. The other uterine horn is stripped of serosa and the opposing square centimeter of parietal peritoneum is excised but not treated with the composition of Example 3. The composition of Example 3 is rendered thermally- irreversible by contact with the bodily fluids of the rats. Thereafter, the treated portions of the uterine horn and the untreated portions of the uterine horn are attached within 0.5 centimeters of the surgical injury to the peritoneal parietal area by single 3-0 VICRYL ligature suture. This is done to insure that the injured surface of the uterine horn remains in close proximity to the surgical injury of the parietal area of the peritoneum until re-peritonealization occurs. The abdominal wall is closed with a single layer of interrupted 0—0 VICRYL suture and 21 days later, the rats are sacrificed and the abdomen examined for the presence of adhesions. It is noted that adhesions develop where surgically injured areas of the uterine horn and parietal peritoneum are left untreated, while adhesions fail to develop where the injured areas are treated with the composition of Example 3.

EXAMPLE 5

Ion exchange resin beads sold under the trade name Duolite were treated so as to incorporate calcium by first treating a 30 gram sample of the ion exchange resin with a solution of 0.1 molar hydrochloric acid so as to allow the exchange of protons for sodium. After three washings with 0.1 molar hydrochloric acid, the beads were washed with water and then washed twice with a 2% aqueous solution of calcium chloride. Each of the washing steps took place over a period of 16 hours (overnight). The beads were thereafter filtered and washed with water utilizing coarse filter paper and a Buchner glass filter assembly. The beads were then left overnight in a desiccator to dry.

The dried beads of ion exchange resin which were obtained were utilized in the amount of 2 grams to fill a first compartment (close to the needle of the syringe) of a glass syringe utilized to apply liquids and dry materials. The syringe is sold under the tradename Hypak. Into the second compartment of the syringe, there was placed the solution of Example 2. Pushing the plunger of the syringe forward resulted in mixing the solution of Example 2 with the ion exchange beads. After 5 to 10 minutes subsequent to mixing, the mixture was expelled from the syringe. After an additional 15 minutes, the expelled material formed a thermo-irreversible film on the substrate on which it was expelled.

While this invention has been described with reference to certain specific embodiments, it will be recognized by those skilled in the art that many variations are possible without departing from the scope and spirit of the invention, and it will be understood that it is intended to cover all changes and modifications of the invention, disclosed herein for the purposes of illustration, which do not constitute departures from the spirit and scope of the invention.

The embodiments of the invention in which an exclusive property or privilege is claimed are defined as follows:

1. A process for reducing post-surgical adhesion formation/reformation following injury to organs situated in mammalian body spaces comprising separating said organs from adjacent mammalian tissue with an effective adhesion reducing amount of a thermally-irreversible aqueous gel composition consisting essentially of water and a mixture of at least one ionic polysaccharide,
   (A) at least one polyoxyalkylene block copolymer of the formula $$Y[(A)_n—E—H]_x \qquad (I)$$

wherein A is an oxyalkylene moiety having an oxygen/carbon atom ratio of less that 0.5, x is at least 1, Y is derived from water or an organic compound containing x reactive hydrogen atoms, E is a polyoxyethylene moiety, n has a value such that the average molecular weight of A is at least about 500 to about 900, as determined by the hydroxyl number of an intermediate, $$Y[(A)_n—H]_x \qquad (II)$$

and the total average molecular weight of the copolymer is at least about 5000 and
   (B) optionally, a latent form of at least one counter-ion capable of thermo-irreversibly gelling said composition.

2. The process of claim 1, wherein Y in said formulas I and II is a water soluble organic compound having 1-6 carbon atoms, and said copolymer is selected from the group consisting of a polyoxyethylene-polyoxybutylene block copolymer, a polyoxyethylene-polyoxypropylene block copolymer and mixtures thereof, wherein the polyoxyethylene moiety constitutes at least 70% by weight of the polymer.

3. The process of claim 2, wherein said copolymer is selected from block copolymers which form aqueous gels at a concentration of about 10-40% by weight of the total weight of said composition.

4. The process of claim 3, wherein said Y is a compound selected from the group consisting of propylene glycol, glycerin, pentaerythritol, trimethylolpropane, ethylenediamine, and mixtures thereof, and wherein said optional counter-ion is, if present, in latent form as a microencapsulated component or incorporated with an ion exchange resin.

5. The process of claim 4, wherein Y is derived from propylene glycol, A is the residue of propylene oxide, and the intermediate of Formula II has an average molecular weight of at least about 900.

6. The process of claim 4, wherein Y is derived from butylene glycol, A is the residue of butylene oxide, and the intermediate of Formula II has an average molecular weight of at least about 500.

7. The process of claim 5, wherein said polymer has the formula $$HO(C_2H_4O)_b(C_4H_8O)_a(C_2H_4O)_bH \qquad (III)$$

wherein in III, a and b are integers such that the hydrophobe base represented by $(C_4H_8O)^a$ has a molecular weight of at least about 1000, as determined by hydroxyl number, the polyoxyethylene chain constitutes at least about 60% by weight of the copolymer, and the copolymer has a total average molecular weight of at least about 5,000, or $$HO(C_2H_4O)_b(C_3H_6O)_a C_2H_4O)_bH \qquad (IV)$$

wherein in IV, a and b are integers such that the hydrophobe base represented by $(C_3H_6O)^a$ has a molecular weight of at least about 1500 average molecular weight, as determined by hydroxyl number, the polyoxyethylene chain constitutes at least about 60% by weight of the copolymer, and the copolymer has a total average molecular weight of at least about 5,000 or wherein in V, a and b are integers such that the copolymer has a hydrophobe molecular weight of at least about 2000, a hydrophile content of at least about 60%, and a total average molecular weight of at least about 5,000.

8. The process of claim 7, wherein said copolymer is $$H[OCH_2CH_2]_{49}[OCHCH_2]_{67}[OCH_2CH_2]_{49}OH \qquad (VI)$$
(with CH$_3$ branch)

9. The process of claim 8, wherein said copolymer is present in a concentration of about 15% to about 30% by weight of the total weight of said composition, said composition forms a thermally-irreversible alginate gel upon contact with said mammalian tissue or said optional counter-ion which is selected from the group consisting of calcium, strontium, aluminum and mixtures thereof, said composition is isotonic and includes a pharmaceutically acceptable buffer, said counter-ion, if present, is in latent form as a microencapsulated component or incorporated with an ion exchange resin, and said organs are situated in the peritoneal, pelvic, or pleural cavity.

10. The process of claim 8, wherein said polyoxyalkylene block copolymer is present in the amount of about 15 to about 30% by weight of said aqueous composition, said composition forms a thermally-irreversible gel upon contact with said mammalian tissue or said optional counter-ion, said composition is isotonic, said counter-ion, if present, is in latent form and present in an ionic compound as a microencapsulated component or present as an anion in an ion exchange resin, said counter-ion is the anion of an ammonium or metal salt which anion is selected from the group consisting of the phosphates, metaphosphates, pyrophosphates, tripolyphosphates, and mixtures thereof, and said ionic polysaccharide is chitosan.

11. A thermally-irreversible, aqueous gel composition for reducing post-surgical adhesion formation/reformation following injury to organs situated in mammalian body spaces, said composition consisting essentially of water, a mixture of at leas tone ionic polysaccharide,
  (A) at least one polyoxyalkylene block copolymer of the formula $$Y[(A)_n\text{—}E\text{—}H]_x \qquad (I)$$

wherein A is a polyoxyalkylene moiety having an oxygen/carbon atom ratio of less than 0.5, x is at least 2, Y is derived from water or an organic compound containing x reactive hydrogen atoms, E is a polyoxyethylene moiety constituting at least about 60% by weight of the copolymer, n has a value such that the average molecular weight of A is at least about 500 to about 900, as determined by the hydroxyl number of an intermediate, $$Y[(A)_n\text{—}_H]_x \qquad (II)$$

and the total average molecular weight of the copolymer is at least about 5000,
  (B) optionally, an additive selected from the group consisting of a humectant, a bactericide, a bacteriostatic agent, an agent to prevent leucocyte migration into an area of surgical injury, a fibrinolytic agent, and mixtures thereof, and
  (C) optionally, a latent form of at least one counter-ion for rendering the mixture thermally-irreversible.

12. The composition of claim 11, wherein said copolymer is prepared using a water soluble organic compound initiator (Y) having 1 to about 6 carbon atoms.

13. The composition of claim 12, wherein said polyoxyalkylene moiety is derived from an alkylene oxide selected from the group consisting of butylene oxide, propylene oxide, and mixtures thereof and Y is derived from an organic compound selected from the group consisting of propylene glycol, glycerin, pentaerythritol, trimethylolpropane, ethylenediamine and mixtures thereof.

14. The composition of claim 13, wherein said humectant is, if present, utilized in the amount of about 0.5% to about 10% by weight of the total weight of the composition and is selected from the group consisting of propylene glycol, glycerin, sorbitol, and mixtures thereof, and wherein said optional counter-ion is in latent form and present as an ionic compound as a microencapsulated component or present as an ion in an ion exchange resin.

15. The composition of claim 14, wherein said copolymer is a polyoxyethylene-polyoxypropylene block copolymer wherein said polyoxyethylene moiety constitutes at least about 70% by weight of the copolymer, the average molecular weight of (A) in Formula I is at least about 1200, and the total molecular weight of the block copolymer is at least about 10,000.

16. The composition of claim 15, wherein the intermediate of Formula II is prepared by initiation with propylene glycol and has a molecular weight of at least about 1500 and said humectant is propylene glycol.

17. The composition of claim 16, wherein said copolymer has the formula:

$$HO(C_2H_4O)_b(C_4H_8O)_a C_2H_4O)_b H \qquad (III)$$

wherein in III, a and b are integers such that the hydrophobe base represented by $(C_4H_8O)^a$ has a molecular weight of at least about 500 as determined by hydroxyl number, the polyoxyethylene chain constituting at least about 70% by weight of the copolymer, and the copolymer having a total average molecular weight of at least about 15,000, or $$HO(C_2H_4O)_b(C_3H_6O)_a(C_2H_4O)_b H \qquad (IV)$$

wherein in IV a and b are integers such that the hydrophobe base represented by $(C_3H_6O)^a$ has a molecular weight of at least about 900 average molecular weight, as determined by hydroxyl number, the polyoxyethylene chain constitutes at least about 70% by weight of the copolymer, and the copolymer having a total average molecular weight of at least about 15,000 or wherein in V, a and b are integers such that the copolymer has a hydrophobe molecular weight of at least about 1500, a hydrophile content of at least about 70%, and a total average molecular weight of at least about 15,000.

18. The composition of claim 17, wherein said polyoxyalkylene block copolymer is $$H[OCH_2CH_2]_{49}[OCHCH_2]_{67}[OCH_2CH_2]_{49}OH \qquad (VI)$$
$$\quad\quad\quad\quad\quad\quad\quad\; |$$
$$\quad\quad\quad\quad\quad\quad\quad CH_3$$

present in the amount of about 10 to about 40% by weight of the total weight of said composition.

19. The composition of claim 18, wherein said polyoxyalkylene block copolymer is present in the amount of about 15 to about 30% by weight in said aqueous composition, said aqueous composition forms a thermally-irreversible alginate gel upon contact with mammalian tissue or said optional counter-ion, which is selected from the group consisting of calcium, strontium, aluminum, and mixtures thereof, said composition is isotonic and said counter-ion is present as a microencapsulated component or incorporated with an ion exchange resin, and said organs are situated in the peritoneal, pelvic, or pleural cavity.

20. The composition of claim 18, wherein said composition forms a thermally-irreversible gel upon contact with mammalian tissue or a counter-ion, said counter-ion is the anion of an ammonium or metal salt selected from the group consisting of phosphates, metaphosphates, pyrophosphates, tripolyphosphates, and mixtures thereof, said ionic polysaccharide is chitosan, and said counter-ion is in latent form and present as an ionic compound as a microencapsulated component or present as an anion in an ion exchange resin.

21. A process for reducing post-surgical adhesion formation/reformation following injury to organs situated in mammalian body spaces comprising separating said organs from adjacent tissue with an effective amount of a thermally- irreversible aqueous gel composition consisting essentially of water and a mixture of at least one ionic polysaccharide, at least one optional counter-ion, present in latent form, at least one surfactant, and at least one polyoxyalkylene polyether, said polyether having a molecular weight of about 10,000 to about 100,000, which is selected from the group consisting of (A) polyoxyalkylene polyethers prepared by reacting ethylene oxide and at least one lower alkylene oxide having 3 to 4 carbon atoms with at least one active hydrogen-containing compound having from 3 to 10 carbon atoms and from 3 to 6 active hydrogens to prepare a heteric or block copolymer intermediate and further reacting said copolymer intermediate with at least one alpha-olefin oxide having an average carbon chain length of about 20 to about 45 aliphatic carbon atoms and wherein said alpha-olefin oxide is present in the amount of about 0.3 to 10 percent by weight based upon the total weight of said polyether.

(B) polyoxyalkylene polyethers prepared by reacting ethylene oxide with at least one active hydrogen-containing compound having from 2 to 10 carbon atoms and from 2 to 6 active hydrogens to prepare a homopolymer intermediate and further reacting said homopolymer with at least one alpha-olefin oxide having an average carbon chain length of about 20 to 45 aliphatic carbon atoms and wherein said alpha-olefin oxide is present in the amount of about 0.3 to 10 percent by weight based on the total weight of said polyether.

22. The process of claim 21, wherein said polyether is prepared using a heteric copolymer intermediate.

23. The process of claim 22, wherein said polyether is prepared using an alpha-olefin oxide having an average carbon chain length of about 20 to 30 carbon atoms, present in the amount of about 0.3 to 10 percent of the total weight of said polyether.

24. The process of claim 23, wherein said polyether contains a proportion of ethylene oxide residue to the residue of said lower alkylene oxide of 70 to about 90 percent by weight of ethylene oxide residue to about 30 to about 10 percent by weight of said lower alkylene oxide residue.

25. The process of claim 24, wherein said polyether is prepared using propylene oxide as the lower alkylene oxide.

26. The process of claim 21, wherein said polyether is prepared using a block copolymer intermediate.

27. The process of claim 26, wherein said polyether is prepared using an alpha-olefin oxide having an average carbon chain length of about 20 to 30 carbon atoms, present in the amount of about 0.3 to 10 percent of the total weight of said polyether.

28. The process of claim 27, wherein said polyether is prepared using a proportion of ethylene oxide residue to the residue of said lower alkylene oxide of from about 70 to about 90 percent by weight of ethylene oxide residue to about 30 to about 10 percent by weight of said lower alkylene oxide residue.

29. The process of claim 28, wherein said polyether is prepared using propylene oxide as the alkylene oxide and said aqueous composition forms a thermally-irreversible aqueous gel upon contact with mammalian body tissue and/or said optional counter-ion, said ionic polysaccharide is an alginate, and said organs are situated in the peritoneal, pelvic, or pleural cavity.

30. The process of claim 21, wherein said polyether is polyether (B) of claim 19.

31. The process of claim 30, wherein said polyether is prepared using an alpha-olefin oxide having an average carbon chain length of about 20 to 30 carbon atoms, present in the amount of about 0.3 to 10 percent of the total weight of said polyether, said composition forms a thermally-irreversible, aqueous gel upon contact with mammalian body tissue or said optional counter-ion which is selected from the group consisting of calcium, strontium, aluminum, and mixtures thereof, said composition is isotonic and includes a pharmaceutically acceptable buffer, said counter-ion, if present, is in latent form as a microencapsulated component or incorporated with an ion exchange resin, said ionic polysaccharide is an alginate, and said organs are situated in the peritoneal, pelvic, or pleural cavity.

32. The process of claim 30, wherein said polyether is prepared using an alpha-olefin oxide having an average carbon chain length of about 20 to 30 carbon atoms, present in the amount of about 0.3 to 10 percent by weight of the total weight of said polyether, said composition is isotonic and forms a thermally-irreversible gel upon contact with mammalian tissue or a counter-ion, said counter-ion is the anion of an ammonium or metal salt which anion is selected from the group consisting of the phosphates, metaphosphates, pyrophosphates, tripolyphosphates, and mixtures thereof, said ionic polysaccharide is chitosan, and said counter-ion is in latent form and present as an ionic compound as a microencapsulated component or present as an anion in an ion exchange resin.

33. A thermally-irreversible aqueous gel composition for reducing post-surgical adhesion formation/reformation following injury to organs situated in mammalian body spaces, said composition consisting essentially of water, a mixture of at least one ionic polysaccharide, at least one surfactant, and at least one polyether having a molecular weight of about 10,000 to about 100,000, which is selected form the group consisting of (A) polyoxyalkylene polyethers prepared by reacting ethylene oxide and at least one lower alkylene oxide having 3 to 4 carbon atoms with at least one active hydrogen-containing compound having from 3 to 10 carbon atoms and from 3 to 6 active hydrogens to prepare a heteric or block copolymer intermediate and further reacting said copolymer intermediate with at least one alpha-olefin oxide having an average carbon chain length of about 20 to about 45 aliphatic carbon atoms and wherein said alpha-olefin oxide is present in the amount of about 0.3 to 10 percent by weight based upon the total weight of said polyether and () polyoxyalkylene polyethers prepared by reacting ethylene oxide with at least one active hydrogen-containing compound having from 2 to 10 carbon atoms and from 2 to 6 active hydrogens to prepare a homopolymer intermediate and further reacting said homopolymer with at least one alpha-olefin oxide having an average carbon chain length of about 20 to 45 aliphatic carbon atoms and wherein said alpha-olefin oxide is present in the amount of about 0.3 to 10 percent by weight based on the total weight of said polyether and (C) optionally, an additive selected from the group consisting of a humectant, a bactericide, a bacteriostatic agent, an agent to prevent leucocyte migration into an area of surgical injury, a fibrinolytic agent, and mixtures thereof, and (D) optionally, a latent form of a counter-ion capable of rendering the mixture thermally-irreversible.

34. The composition of claim 33, wherein said polyether is prepared using a heteric copolymer intermediate.

35. The composition of claim 34, wherein said polyether is prepared using an alpha-olefin oxide having an average carbon chain length of about 20 to 30 carbon atoms, present in the amount of about 0.3 to 10 percent of the total weight of said polyether.

36. The composition of claim 35, wherein the polyether is prepared using a proportion of ethylene oxide residue to the residue of said lower alkylene oxide of about 70 to about 90 percent by weight of ethylene oxide residue to about 30 to about 10 percent by weight of said lower alkylene oxide residue.

37. The composition of claim 36, wherein said polyether is prepared using propylene oxide as the lower alkylene oxide.

38. The composition of claim 33, wherein said polyether is prepared using a block copolymer intermediate.

39. The composition of claim 38, wherein said polyether is prepared using an alpha-olefin oxide having an average carbon chain length of about 20 to 30 carbon atoms, present in the amount of about 0.3 to 10 percent of the total weight of said polyether.

40. The composition of claim 39, wherein the polyether is prepared using a proportion of ethylene oxide residue to the residue of said lower alkylene oxide of about 70 to about 90 percent by weight of ethylene oxide residue to about 30 to about 10 percent by weight of said lower alkylene oxide residue.

41. The composition of claim 40, wherein said polyether is prepared using propylene oxide as the lower alkylene oxide.

42. The composition of claim 30, wherein said polyether is polyether (B) of claim 30.

43. The composition of claim 42, wherein said polyether is prepared using an alpha-olefin oxide having an average carbon chain length of about 20 to 30 carbon atoms, present in the amount of about 0.3 to 10 percent by weight of the total weight of said polyether, said composition forms a thermally-irreversible alginate gel composition upon contact with mammalian body tissue and/or said optional counter-ion selected from the group consisting of calcium, strontium, aluminum, and mixtures thereof, said composition is isotonic, said counter-ion, if present, is in latent form and present at an ionic compound as a microencapsulated component or present as a cation in an ion exchange resin, and said organs are situated in the peritoneal, pelvic, or pleural cavity.

44. The composition of claim 42, wherein said polyether is prepared using an alpha-olefin oxide having an average carbon chain length of about 20 to 30 carbon atoms, present in the amount of about 0.3 to 10 percent by weight of the total weight of said polyether, said composition is isotonic, said counter-ion is the anion of an ammonium or metal salt which anion is selected from the group consisting of the phosphates, metaphosphates, pyrophosphates, tripolyphosphates, and mixtures thereof, said ionic polysaccharide is chitosan, and said counter-ion is in latent form and present as an ionic compound as a microencapsulated component or present as an anion in an ion exchange resin.

* * * * *